(12) United States Patent
Wang et al.

(10) Patent No.: US 12,703,924 B2
(45) Date of Patent: Aug. 11, 2026

(54) ANTIOXIDANT CULTURE METHOD AND ANTIOXIDANT AUXILIARY EQUIPMENT

(71) Applicant: National Pingtung University of Science and Technology, Pingtung (TW)

(72) Inventors: Hsian-Yu Wang, Pingtung (TW); Yu-Jing Zeng, Pingtung (TW)

(73) Assignee: National Pingtung University of Science and Technology, Pingtung (TW)

( * ) Notice: Subject to any disclaimer, the term of this patent is extended or adjusted under 35 U.S.C. 154(b) by 789 days.

(21) Appl. No.: 18/146,761

(22) Filed: Dec. 27, 2022

(65) Prior Publication Data

US 2024/0026554 A1 Jan. 25, 2024

(30) Foreign Application Priority Data

Jul. 19, 2022 (TW) ................................. 111127031

(51) Int. Cl.
*C25B 15/08* (2006.01)
*C12M 1/00* (2006.01)
(Continued)

(52) U.S. Cl.
CPC ........... *C25B 15/081* (2021.01); *C12M 29/00* (2013.01); *C12M 41/34* (2013.01); *C12N 7/00* (2013.01);
(Continued)

(58) Field of Classification Search
None
See application file for complete search history.

(56) References Cited

U.S. PATENT DOCUMENTS

2013/0203953 A1* 8/2013 Pereira ...................... C25B 3/23 585/16
2015/0228996 A1* 8/2015 Armiger ................ C25B 15/02 429/2

(Continued)

FOREIGN PATENT DOCUMENTS

CN 110528017 B 1/2021
CN 213416792 U 6/2021

OTHER PUBLICATIONS

Hu et al., Molecular hydrogen: A potential radioprotective agent, Biomedicine & Pharmacotherapy 130 (2020) 110589 (Year: 2020).*

(Continued)

*Primary Examiner* — Holly Kipouros
(74) *Attorney, Agent, or Firm* — Troutman Pepper Locke LLP; Tim Tingkang Xia, Esq.

(57) ABSTRACT

The present invention relates to an antioxidant culture method and antioxidant auxiliary equipment. The antioxidant cultivation method comprises: providing an electrolytic hydrogen generator comprising an anode, a cathode and a membrane between the cathode and the anode, the electrolytic hydrogen generator being connected with a bioreactor; inputting the culture medium in the bioreactor to the cathode and inputting a pure water to the anode; and providing an electric current to the electrolytic hydrogen generator to output a hydrogen from the cathode so as to dissolve the hydrogen in the culture medium of the bioreactor.

19 Claims, 8 Drawing Sheets

Specification includes a Sequence Listing.

(51) Int. Cl.

| | |
|---|---|
| ***C12M 1/34*** | (2006.01) |
| ***C12N 7/00*** | (2006.01) |
| ***C25B 1/04*** | (2021.01) |
| ***C25B 9/19*** | (2021.01) |
| ***C25B 15/029*** | (2021.01) |
| ***H01M 8/0656*** | (2016.01) |
| ***H01M 8/1018*** | (2016.01) |
| *H01M 8/10* | (2016.01) |

(52) U.S. Cl.

CPC .................. *C25B 1/04* (2013.01); *C25B 9/19* (2021.01); *C25B 15/029* (2021.01); *H01M 8/0656* (2013.01); *H01M 8/1018* (2013.01); *C12N 2760/20051* (2013.01); *H01M 2008/1095* (2013.01)

(56) References Cited

U.S. PATENT DOCUMENTS

2016/0032467 A1* 2/2016 Kim .......................... C25B 9/73 204/263

2024/0294410 A1* 9/2024 Ostermeyer ............ C02F 3/005

OTHER PUBLICATIONS

Hoedemakers et al., Study of the bubble behavior in alkaline water electrolysis, Jan. 27, 2021, student thesis Eindhoven University of Technology (Year: 2021).*

Lee et al., Hydrogen-rich medium protects mouse embryonic fibroblasts from oxidative stress by activating LKB1-AMPK-FoxO1 signal pathway, Biochemical and Biophysical Research Communications 491 (2017) 733e739 (Year: 2017).*

* cited by examiner

ANTIOXIDANT CULTURE METHOD AND ANTIOXIDANT AUXILIARY EQUIPMENT

CROSSED-REFERENCE TO RELATED APPLICATION

This application claims priority to and the benefit of Taiwan Patent Application No. 111127031, filed on Jul. 19, 2022, in the Taiwan Intellectual Property Office, the entire content of which is incorporated herein by reference.

The sequence information contained in the Sequence Listing XML file, with the file name "P22-0121 sequence listing.xml" created on Nov. 16, 2022 and having a file size of 2,825 bytes, is incorporated by reference herein in its entirety.

BACKGROUND OF THE INVENTION

1. Field of the Invention

The present invention relates to an antioxidant culture method and antioxidant auxiliary equipment, especially to an antioxidant culture method and antioxidant auxiliary equipment for a bioreactor.

2. Description of Related Art

Bioreactors provide a wide range of applications, such as bacterial culture for fermentation, scale-up cell cultivation, virus production, recombinant protein production or antibody production. However, it is difficult to develop the scale-up technology in the bioreactor. High yields in small volumetric flasks can be often obtained under laboratory conditions, but when the mass production is conducted in large vessels or various types of bioreactors, problems such as instability or reduced yields make the subsequent process difficult and lead to reduced total production or failed batch. This phenomenon is more common in cell culture reactors for virus production.

Microorganisms or cells need a stable and healthy growth environment, otherwise they cannot perform their functions or achieve optimal production. The control factors of growth environment are such as: temperature, pH value, gas solubility, pressure, etc. There has been considerable researches and solutions on the control of the growth environment in bioreactors. In our previous study, it was found that high-density cell culture increases the oxidative stress of cells, and the increased oxidative stress of cells will lead to senescence and dormancy of cells, resulting in difficulty on replication of the viruses in the cells. Therefore, the virus yield is not stable and there is still no solution to the problem now.

SUMMARY OF THE INVENTION

The present invention provides an antioxidant culture method comprising: providing an electrolysis-based hydrogen generator comprising an anode, a cathode, and a septum between the anode and the cathode; connecting the electrolysis-based hydrogen generator and a bioreactor; inputting a culture medium of the bioreactor to the cathode and inputting a pure water to the anode; and providing a current to the electrolysis-based hydrogen generator to output a hydrogen from the cathode and dissolve the hydrogen in the culture medium of the bioreactor.

The present invention further provides an antioxidant auxiliary equipment which is connected with a bioreactor and comprises: an electrolysis-based hydrogen generator comprising an anode, a cathode connected with the bioreactor and a septum between the anode and the cathode, a culture medium of the bioreactor being inputted into the electrolysis-based hydrogen generator via a first pump; a pure water supply end connected with the anode, pure water in the pure water supply end being inputted into the electrolysis-based hydrogen generator via a second pump; and a power control unit electrically connected with the electrolysis-based hydrogen generator for providing direct current to the electrolysis-based hydrogen generator and controlling the operation of the first pump and the second pump.

The antioxidant culture method and antioxidant auxiliary equipment which provided by the present invention is suitable for applying to the bioreactor due to high biological safety, no drug residue, no toxic by-products and high purity of hydrogen which is generated by the hydrogen production method from water electrolysis applying the hydrogen fuel cell technology. In addition, the method provided by the present invention can control the hydrogen production by controlling the current, which can be easily introduced into the process and avoid the generation of large bubbles in the culture medium, and can simply and effectively adjust the oxidative pressure of the environment.

At the same time, reducing oxidative stress helps to postpone the senescence during cell culture, reduce the antiviral response of cells caused by aging induced by oxidative stress, increase the cell susceptibility to viruses, and improve the utilization of cells by viruses to increase production. Usually, the proportion of cytopathic effect or even cell consumption is positively correlated with the virus yield. The embodiment of the present invention can shorten the occurrence time of cytopathic effect, speed up the production cycle, and then accelerate the viral antigen production speed and cumulatively increase the viral antigen yield, greatly improving the vaccine production process.

8B shows a bar chart of the cell death rate in the hydrogen group and in the hydrogen-free group according to embodiment 3 of the present invention.

Figure 9:
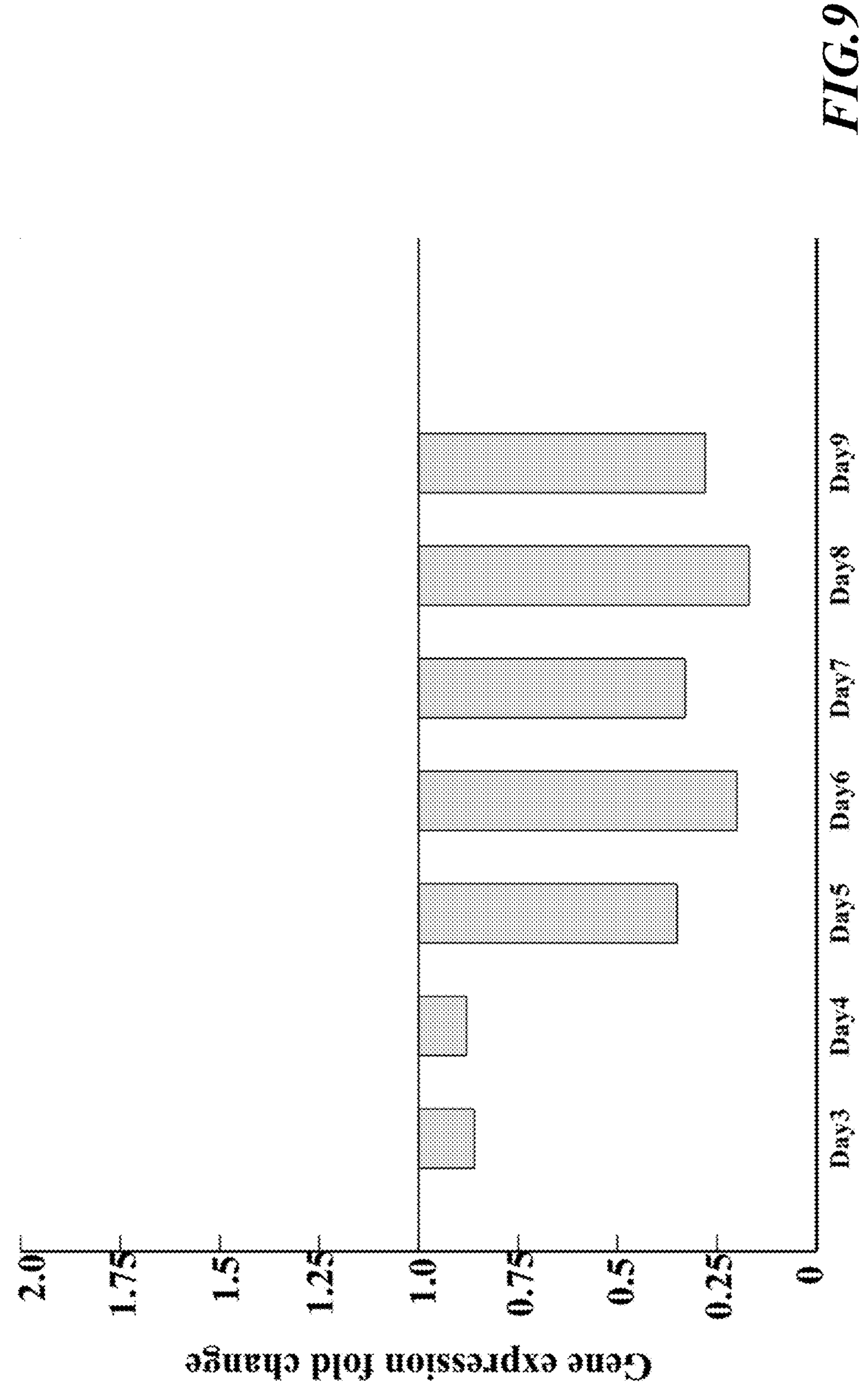

FIG. 9 shows a bar chart of the Cdkn2a(p16) gene expression fold change according to embodiment 3 of the present invention.

DETAILED DESCRIPTION OF THE PREFERRED EMBODIMENTS

Other technical contents, aspects and effects in relation to the present invention can be clearly appreciated through the detailed descriptions concerning the preferred embodiments of the present invention in conjunction with the appended drawings.

Unless otherwise defined herein, all technical and scientific terms used have the same meaning as commonly understood by those skilled in the art to which the present invention belongs.

As used herein, the articles "a", "an" and "any" refer to one or more than one (i.e. at least one) grammatical items. For example, "a component" means a component or more than a component.

The term "about", "approximately" or "nearly" used herein substantially represents the stated value or range within 20%, preferably within 10%, and more preferably within 5%. The digitized quantities provided in the article are approximate value, meaning that if the terms "about", "approximately" or "nearly" are not used, they can be inferred.

The terms "connected" or "arranged" disclosed in the contents of the present specification for describing the structural combination relationship refer to a directly physical connection or an indirectly physical connection through pipeline or conduit and/or by using threads, latches, fasteners, nails, adhesives or high frequency waves or any other feasible approaches.

The terms "electrically connected" disclosed in the contents of the present specification for describing the structural combination relationship refer to the combination of electric power enabling or network communications by using e.g., wires, circuit boards, network cables, Bluetooth or wireless networks or any other feasible approaches.

Figure 1:
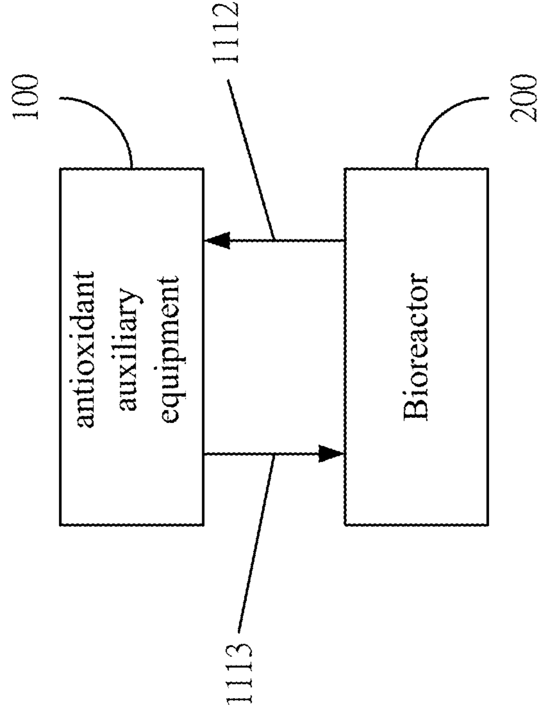
FIG. 1 shows a block diagram of the bioreactor-hydrogen system according to one embodiment of the present invention.

As shown in FIG. 1, the antioxidant auxiliary equipment 100 of the present invention is connected with the bioreactor 200 to form a bioreactor-hydrogen system, so that the antioxidant auxiliary equipment 100 could provide hydrogen to the bioreactor 200. The bioreactor 200 comprises a tidal bioreactor, rotary drum bioreactor, fixed-bed bioreactor, suspension bioreactor, etc.

Figure 2:
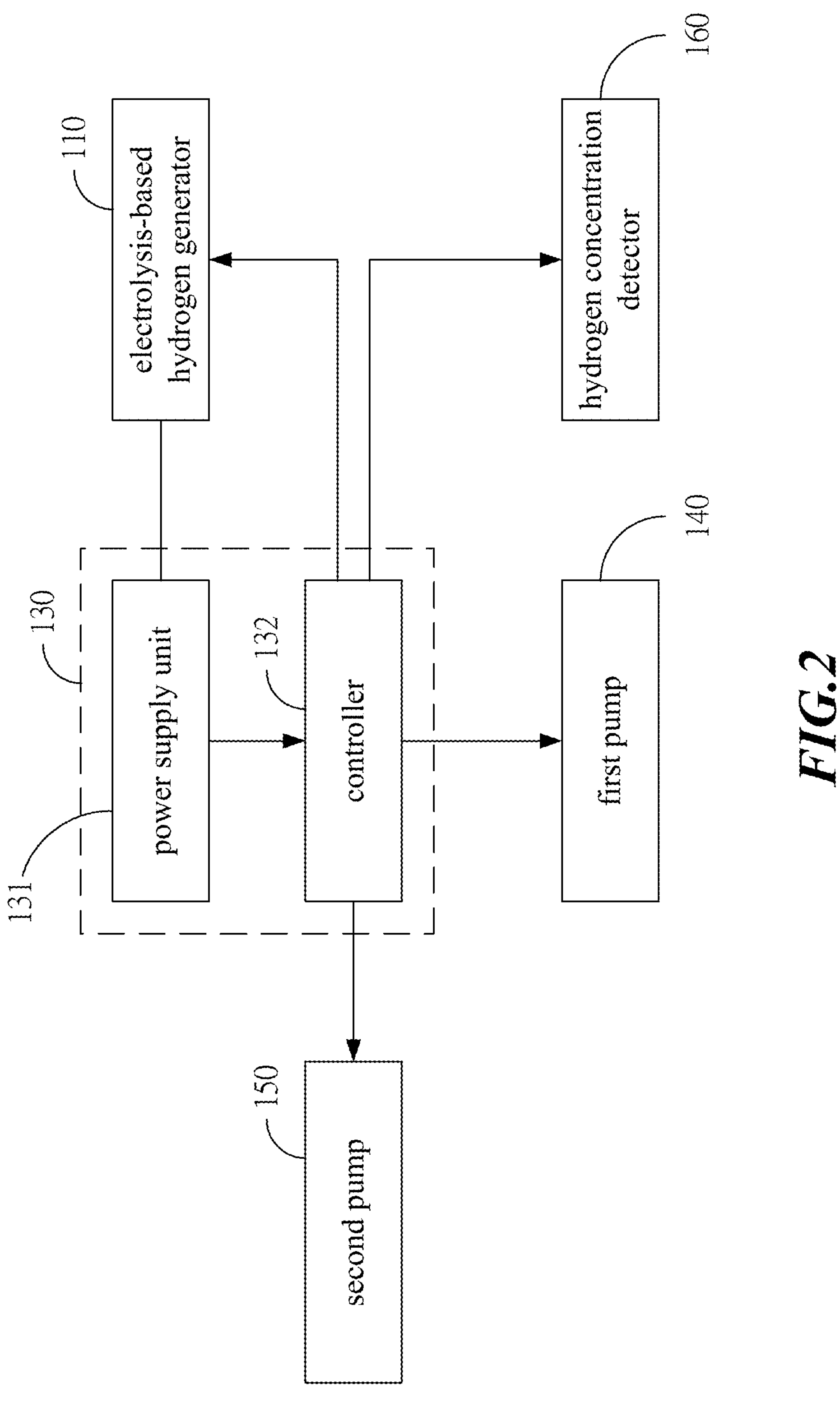
FIG. 2 shows a block diagram of the antioxidant auxiliary equipment according to one embodiment of the present invention.
Figure 3:
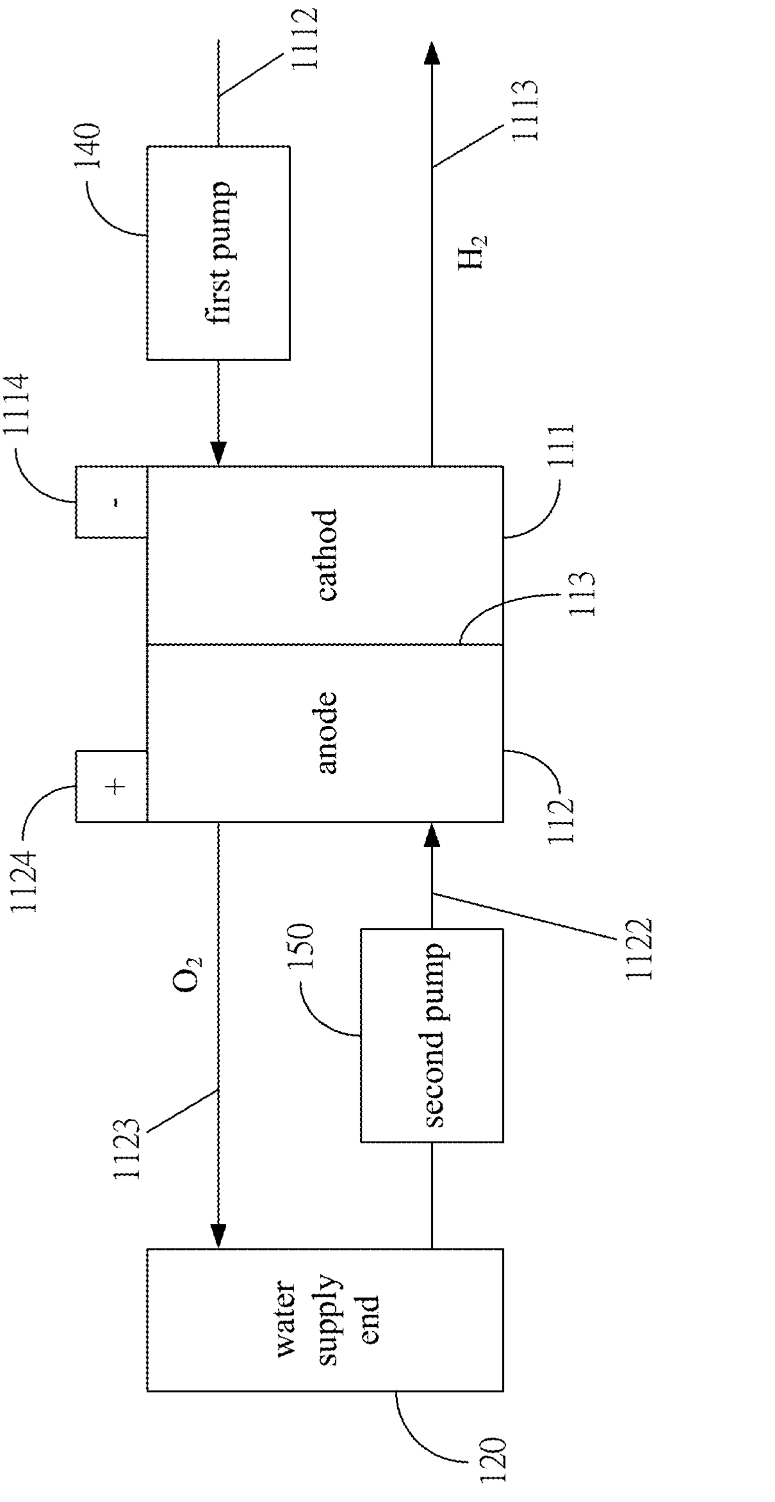
FIG. 3 shows an illustrative diagram for the pipelines of the antioxidant auxiliary equipment according to one embodiment of the present invention.

As shown in FIG. 2 and FIG. 3, the antioxidant auxiliary equipment 100 of the present invention comprises an electrolysis-based hydrogen generator 110, a pure water supply end 120 and a power control unit 130. The electrolysis-based hydrogen generator 110 comprises a cathode 111, an anode 112 and a septum 113. The septum 113 is arranged between the cathode 111 and the anode 112 and is a polymer membrane such as a fluorine-containing polymer membrane. The septum 113 has excellent airtightness, and can separate oxygen and hydrogen to prevent the oxygen from burning at high temperature. The electrolysis-based hydrogen generator 110 could be a proton exchange membrane fuel cell (PEMFC). The polymer membrane is a proton exchange membrane, and pure water can be directly used for solid-state electrolysis. The pure water in the anode 112 is electrolyzed into water and hydrogen ions by reverse engineering. ($2H_2O \rightarrow O_2+4H^++4e^-$), and hydrogen gas ($4H^++4e^- \rightarrow 2H_2$) is formed at the cathode 111, and no toxic by-products such as chlorine gas or ozone are generated.

The pure water supply end 120 is connected with the anode 112, and inputted the pure water inside the pure water supply end 120 into the electrolysis-based hydrogen generator 110 via a second pump 150. The anode 112 comprises a third pipeline 1122, a fourth pipeline 1123 and an anode contact 1124. The third pipeline 1122 and the fourth pipeline 1123 are connected with the pure water supply end 120. The third pipeline 112 is provided with a second pump 150 and the fourth pipeline 1123 is used for outputting oxygen gas to the pure water supply end 120.

The cathode 111 is connected with the bioreactor 200 and outputted the hydrogen gas to the bioreactor 200. The culture medium of the bioreactor 200 is inputted into the electrolysis-based hydrogen generator 110 via a first pump 140. The cathode 111 comprises a first pipeline 1112, a second pipeline 1113 and a cathode contact 1114. The first pipeline 1112 and the second pipeline 1113 are connected with the bioreactor 200 and the first pipeline 1112 is provided with the first pump 140. The second pipeline 1113 is used for outputting hydrogen gas to the bioreactor 200. The anode contact 1124 and the cathode contact 1114 are electrically connected to the power control unit 130.

The power control unit 130 converts the alternating current to direct current and provides direct current to the electrolysis-based hydrogen generator 110 electrically connected thereto, and controls the operation of the first pump 140 and the second pump 150. The power control unit 130 comprises a power supply unit 131 and a controller 132. The positive electrode of the power supply unit 131 is electrically connected to the anode contact 1124 via the controller 132 and the cathode contact 1114 is electrically connected to the negative electrode of the power supply unit 131, so that the controller 132 can control the start-up of the electrolysis-based hydrogen generator 110. The controller 132 is also responsible for controlling the operations of the first pump 140 and the second pump 150.

The controller 132 is electrically connected with the first pump 140 and the second pump 150. The controller 132 may include a central processing unit (CPU), a system on chip (SOC), or other programmable general-purpose or special-purpose microprocessors, digital signal processors (DSP), programmable controller, other similar processing devices or a combination of these devices, but the present invention is not limited thereto.

The antioxidant auxiliary device 100 may further comprise a hydrogen concentration detector 160 which is arranged in the culture medium in the bioreactor 200 and is connected to the power control unit 130 for measuring the hydrogen concentration of the culture medium and adjusting the power control unit 130 according to the comparison result of the hydrogen concentration of the culture medium and a default value. The hydrogen concentration detector 160 may be a dissolved hydrogen meter. When the hydrogen concentration is lower than the default value, the power control unit 130 increases the activation frequency of the current. When the hydrogen concentration is higher than the default value, the power control unit 130 maintains or decreases the activation frequency of current.

The antioxidant culture method applying the electrolysis-based hydrogen generator of the present invention comprises: providing an electrolysis-based hydrogen generator comprising an anode, a cathode, and a septum between the anode and the cathode; connecting the electrolysis-based hydrogen generator and a bioreactor; inputting a culture medium of the bioreactor to the cathode and inputting a pure water to the anode; and providing a current to the electrolysis-based hydrogen generator to output a hydrogen gas from the cathode, to dissolve the hydrogen gas in the culture medium of the bioreactor, and to output an oxygen gas from the anode.

In some embodiments, the antioxidant culture method of the present invention further comprises measuring a hydrogen concentration of the culture medium, and raising an activation frequency of the current when the hydrogen concentration is lower than a default value.

In some embodiments, in the step of supplying current to the electrolysis-based hydrogen generator, the activation frequency of the current is set for allowing the hydrogen concentration of the culture medium to reach a maximum stable range, and the setting default value is included in the maximum stable range. The maximum stable range indicates a range that even if the activation frequency of the current is further adjusted upwards, the hydrogen concentration in the culture medium will not continue rising and will fluctuate between the range stably.

The maximum stable range of the hydrogen concentration is related to the type of bioreactor and the cultured microorganisms or cells. In some embodiments, the hydrogen concentration of the culture medium ranges between 0.1 ppm to 1.6 ppm, such as about 0.1 ppm, about 0.2 ppm, about 0.3 ppm, about 0.4 ppm, about 0.5 ppm, about 0.6 ppm, about 0.7 ppm, about 0.8 ppm, about 0.9 ppm, about 1.0 ppm, about 1.1 ppm, about 1.2 ppm, about 1.3 ppm, about 1.4 ppm, about 1.5 ppm, about 1.6 ppm.

In some embodiments, the current is a constant current. According to the formula ($4H^+ + 4e^- \rightarrow 2H_2$), it can be seen that the larger amount of current is, the greater the hydrogen production efficiency will be, resulting in an increase in the amount of bubbles produced. Therefore, providing a suitable and stable current can reduce the generation of large air bubbles. The constant current may not exceed 0.5 amps (A), such as about 0.5 amps, about 0.4 amps, about 0.3 amps, about 0.2 amps, or about 0.1 amps.

In some embodiments, an activation frequency of the current is 1 to 3 times per hour for more than 10 minutes each time. The activation frequency of the current includes but is not limited to 1, 2 or 3 times per hour, and more than 10 minutes each time, such as about 10 minutes, about 15 minutes, about 20 minutes, about 25 minutes, about 30 minutes, about 35 minutes, about 40 minutes or about 45 minutes.

In some embodiments, when the antioxidant culture method is applied in a virus antigen manufacturing procedure, the step of providing a current to the electrolysis-based hydrogen generator comprises two stages which are a first stage and a second stage. The first stage is before the cell is infected with virus and a second stage is after the cell is infected with virus, the first stage and the second stage have different activation frequency of the current. In some embodiments, an activation frequency of the current at the second stage is higher than that at the first stage about 3 times, about 2.5 times, about 2 times or about 1.5 times.

In some embodiments, the activation frequency of the current at the first stage is once per hour for 15 minutes each time, and the activation frequency of the current at the second stage is twice per hour for 15 minutes each time. In some embodiments, the duration of the first stage is proportional to the duration of the second stage. In certain embodiments, the duration of the first stage and the duration of the second stage are 1 day.

In some embodiments, the antioxidant culture method and the antioxidant auxiliary device are applied in a virus antigen manufacturing procedure. The bioreactor may be a tidal bioreactor, and the default value of hydrogen concentration is 0.7 ppm.

In some embodiments, the antioxidant culture method is to connect an auxiliary equipment with the bioreactor to provide the electrolysis-based hydrogen generator for cell culture. The antioxidant auxiliary equipment comprises: the electrolysis-based hydrogen generator, wherein the cathode is connected with the bioreactor, and a culture medium of the bioreactor being inputted into the electrolysis-based hydrogen generator via a first pump and hydrogen gas being outputted from the cathode to the bioreactor; a pure water supply end connected with the anode, pure water in the pure water supply end being inputted into the electrolysis-based hydrogen generator via a second pump; and a power control unit electrically connected with the electrolysis-based hydrogen generator for providing direct current to the electrolysis-based hydrogen generator and controlling the operation of the first pump and the second pump.

In some embodiments, the cathode comprises a first pipeline and a second pipeline. The first pipeline and the second pipeline are connected with the bioreactor and the first pipeline is provided with the first pump. The second pipeline is used for outputting hydrogen gas. The anode comprises a third pipeline and a fourth pipeline. The third pipeline and the fourth pipeline are connected with the pure water supply end. The third pipeline is provided with a second pump and the fourth pipeline is used for outputting oxygen gas. In some embodiments, the cathode further comprises a cathode contact, and the anode further comprises an anode contact. The anode contact and the cathode contact are electrically connected to the power control unit.

In some embodiments, the power control unit comprises a power supply unit and a controller. The positive electrode of the power supply unit is electrically connected to the anode contact via the controller and the cathode contact is electrically connected to the negative electrode of the power supply unit. The controller is electrical connected with the first pump and the second pump.

In some embodiments, the antioxidant auxiliary equipment further comprises a hydrogen concentration detector which is arranged in the culture medium in the bioreactor and is connected to the power control unit for measuring the hydrogen concentration of the culture medium and adjusting the power control unit according to the comparison result of the hydrogen concentration of the culture medium and a default value.

In some embodiments, the electrolysis-based hydrogen generator is a proton exchange membrane fuel cell, and the septum is a polymer membrane.

Example 1 Antioxidant Cell Culture Method

In the pre-experimental treatment, the tubes containing hamster kidney cells (BHK21, BCRC #60041, Taiwan) were thawed. The hamster kidney cells were incubated at 37° C. in an incubator with 5.0% $CO_2$ using MEM culture medium (Invitrogen, Gibco Co. Ltd., New York, USA, with 10% FBS). The hamster kidney cells were incubated in a cell culture flask (175T Flask) for 3 days, and then placed in a roller bottle for expanded culture for 3 days. At the beginning of the experiment, the cells were first transferred to a tidal bioreactor (Bellocell, Taiwan) with a working volume of 500 ml of culture medium for 2 days to adapt to the environment in which the hamster kidney cells could grow to a saturated number of about $3\times10^9$/bottle. The electrolysis-based hydrogen generator was started on day 2 for antioxidant cell culture to regulate cellular oxidative stress. Here, in one embodiment, a tidal bioreactor could be connected to the antioxidant auxiliary equipment of the present invention.

Example 2 Antioxidant Effect Evaluation

The cells were divided into two groups to analyze the antioxidant effect. The cells in the control group did not use the electrolysis-based hydrogen generator (hydrogen-free group), while the cells in the experimental group used the electrolysis-based hydrogen generator to supply hydrogen (hydrogen group). Following Example 1, when the antioxidant auxiliary equipment was turned on on the second day (day 2), hydrogen gas was supplied at the frequency of turning on the current for 15 minutes per hour, the voltage was 3-5V, the constant current was 0.5 A, and the theoretical hydrogen production was about $466\times10^{-5}$ moles per hour. On the third day, the frequency was adjusted to turn on for 15 minutes and turn off for 15 minutes to continuously supply hydrogen gas until the end of the experiment. The voltage was 3~5V, the constant current was 0.5 A, and the theoretical hydrogen production was about $933\times10^{-5}$ moles per hour. The culture medium was replaced on the third day, and the cells were cultured until the eighth day. Cell number, hydrogen concentrations, and reactive oxygen species (ROS) tolerance responses were measured daily.

2.1 Cell Number

Figure 4:
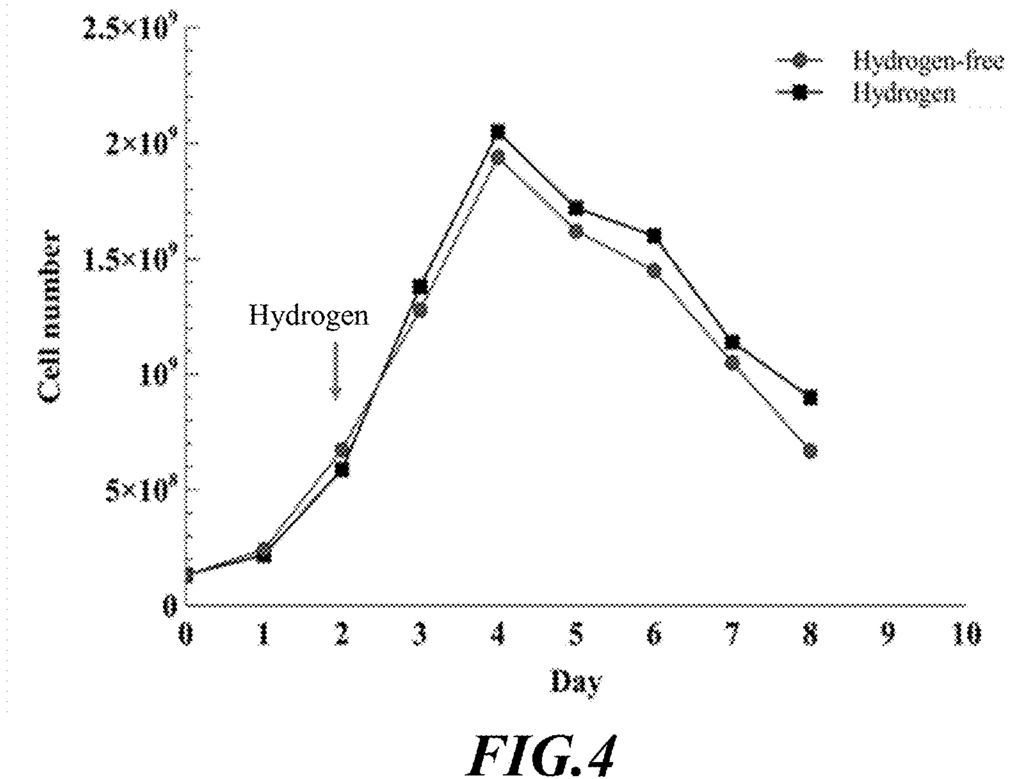
FIG. 4 shows a line chart of cell number change in the hydrogen group and in the hydrogen-free group according to embodiment 2 of the present invention.

The biological carriers in the bioreactors of the experimental group and the control group were collected daily, 1 ml of Crystal Violet Dye (CVD) cell counting dye was added, and the number of cells was counted and recorded using an inverted microscope. As shown in FIG. 4, the antioxidant auxiliary equipment of the experimental group started to supply hydrogen gas on the second day. The growth pattern of cells in the bioreactor with hydrogen and that without hydrogen were the same, which means that molecular hydrogen will not cause damage to cells. The result proved that the antioxidant culture method in the embodiment of the present invention has a high degree of biological safety.

2.2 Hydrogen Concentration

Figure 5:
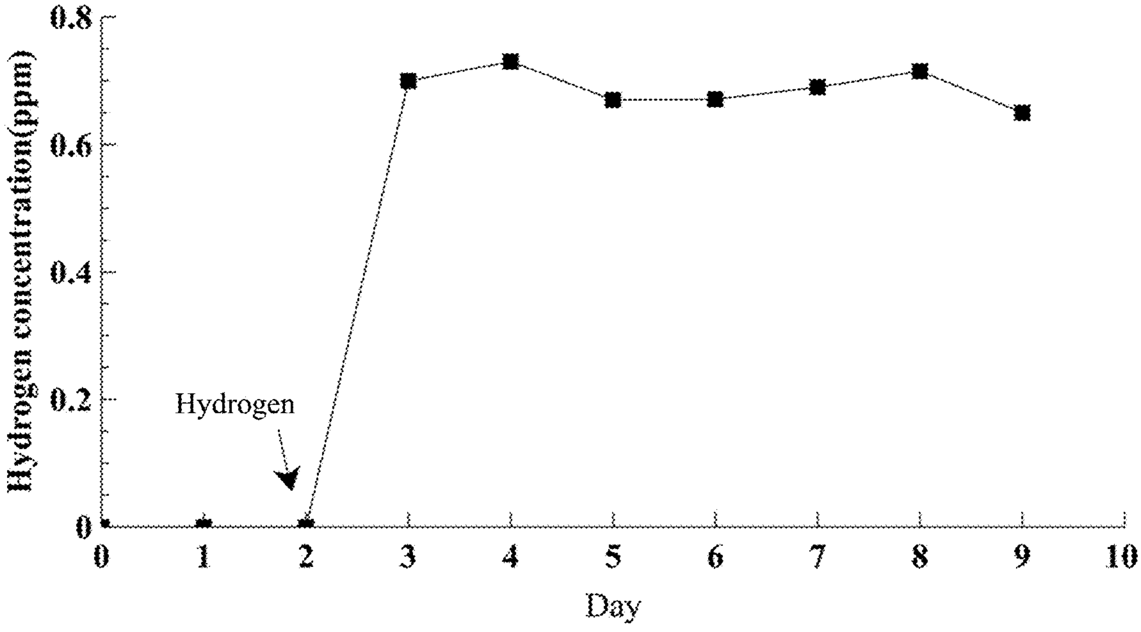
FIG. 5 shows a line chart of hydrogen concentration change of the culture medium in the hydrogen group according to embodiment 2 of the present invention.
Figures 6A, 6B, 6C, 6D:
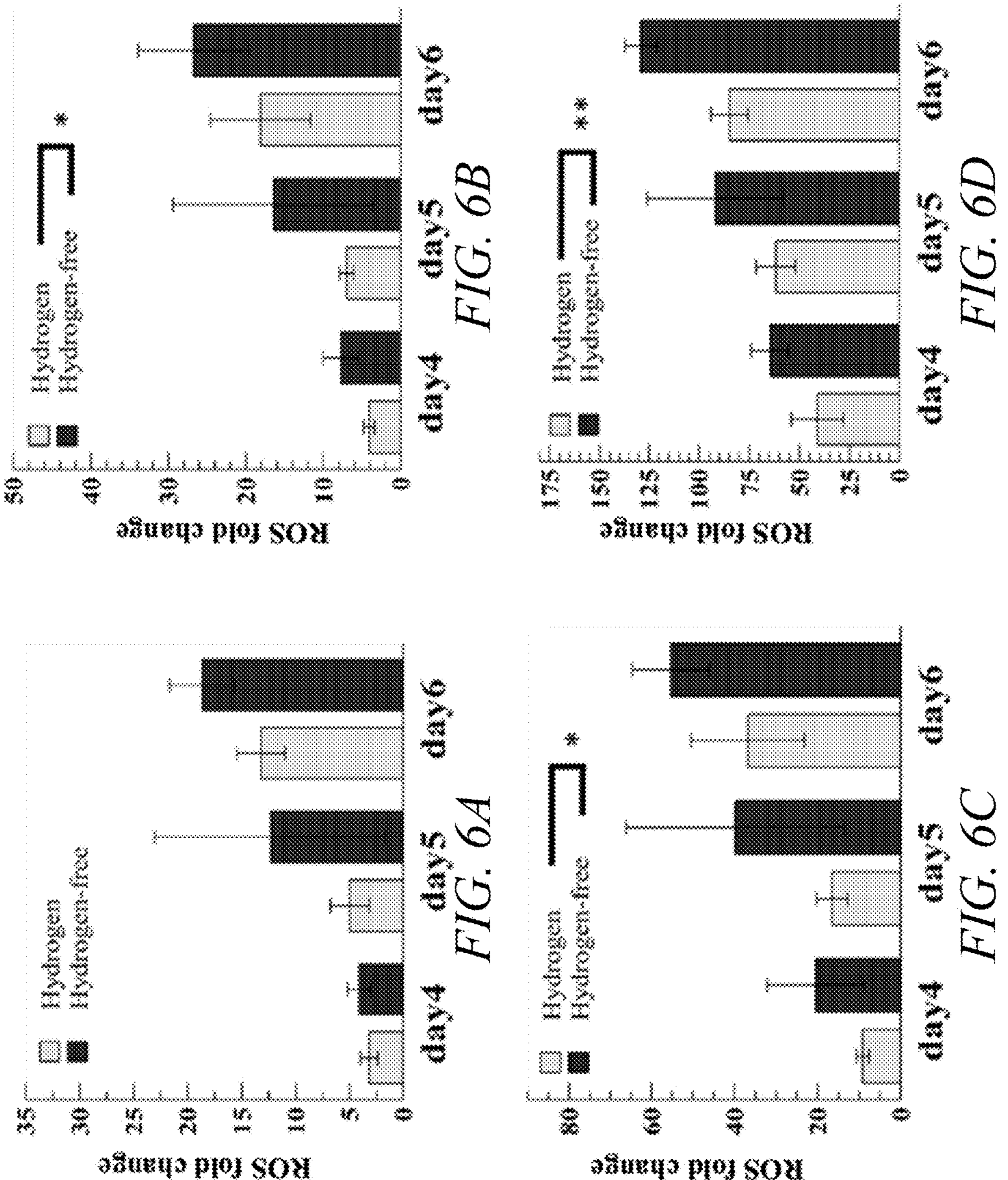
FIGS. 6A, 6B, 6C, and 6D sequentially show a bar chart of the ROS fold change at day 4, day 5, and day 6 after the cell treated with 0 μM $H_2O_2$, 4 μM $H_2O_2$, 10 μM $H_2O_2$, or 20 μM $H_2O_2$ according to embodiment 2 of the present invention (*t-test, $p<0.05$).

This experiment utilized a dissolved hydrogen tester (Twinno, DH30, Taiwan) every day. The antioxidant auxiliary equipment of the experimental group started on the 2nd day to provide hydrogen gas. The culture medium in the experimental group was taken out and inserted into the dissolved hydrogen tester, the measurement was completed when the measured value reached to a stable value, and the measured dissolved hydrogen concentration is recorded daily. As shown in FIG. 5, it could be found that the antioxidant cell culture method of the embodiment of the present invention can stably supply molecular hydrogen to the bioreactor, so that a certain molecular hydrogen concentration is maintained in the culture medium, for example, the maximum stable range is between about 0.6 ppm and about 0.8 ppm. The measured hydrogen concentration of the culture medium in the bioreactor without the supply of molecular hydrogen was about 0.

2.3 Cell ROS Tolerance Response

By adding $H_2O_2$ at concentrations of 0 μM, 4 μM, 10 μM, and 20 μM, the BHK-21 cells ($1\times10^5$/test) in the experimental group and in the control group were induced to undergo oxidation reaction. H2DCFDA was modified by cellular esterases to form a non-fluorescent H2DCF after adding H2DCFDA cell-permeant fluorescence probe. H2DCF was oxidized by intracellular ROS to produce a highly fluorescent product (abcam, ab287839, UK) and was analyzed by flow cytometry (BD Accuri™ C6 Plus Cytometer) on days 4, 5 and 6 after laser excitation ((Ex/Em 495/529 nm) to measure the fluorescent signal activity of reactive oxygen species in each cell so as to know the intracellular ROS tolerance of BHK21 cells. The detected fluorescent signal indicates that the measured cell is a positive cell and in the oxidation state. BD Accuri™ C6 software is used for calculating the number of positive cells, obtain the percentage of positive cells of the total cells in each of the groups (experimental group and control group), and calculate the reactive oxygen species (ROS) fold change=the percentage of positive cells in the experimental group/the percentage of positive cells in the control group.

As shown in FIG. 6A to FIG. 6D, FIG. 6A to FIG. 6D represents the experiment results in which the cells were respectively induced with $H_2O_2$ at low concentration to high concentration (0 μM, 4 μM, 10 μM, 20 μM). The experimental groups that were given molecular hydrogen significantly demonstrated reduced ROS fold change, which indicated that the cells to be tested had higher reactive oxygen species tolerance, that is, antioxidant capacity. Oxidative stress continued to increase over time in the bioreactor, but cells supplied with molecular hydrogen were significantly more tolerant to oxidative stress and had lower oxidative stress than cells not supplied with molecular hydrogen.

Example 3 Mass Production Test for Virus

Following Example 1, the cells were divided into two groups: cells in the control group did not use the electrolysis-based hydrogen generator (hydrogen-free group), and cells in the experimental group used the electrolysis-based hydrogen generator to supply hydrogen gas (hydrogen group). On the second day, the antioxidant auxiliary equipment was started, and hydrogen gas was supplied at the frequency of turning on the current for 15 minutes per hour. On the third day, the frequency of the current was adjusted to the frequency of turning on the current for 15 minutes and turning off the current for 15 minutes. 0.01 MOI bovine epidemic fever virus liquid (virus strain Tn88128, References: Hsieh, Y.-C.; Wang, S.-Y; Lee, Y.-F.; Chen, S.-H.; Mak, P. O. T.; Chu, C.-Y. DNA sequence analysis of glycoprotein G gene of bovine ephemeral fever virus and development of a double oil emulsion vaccine against bovine ephemeral fever. J. Vet. Med. Sci. 2006, 68, 543-548) was used for infecting two groups of cells and the virus was cultured until the eighth day (day 8), the voltage was 3-5V, and the current was 0.5 A. The cell number, hydrogen concentration, viral titer and cell senescence molecular marker Cdkn2a (p16) were measured daily.

3.1 Oxidative Stress Test

Figure 7:
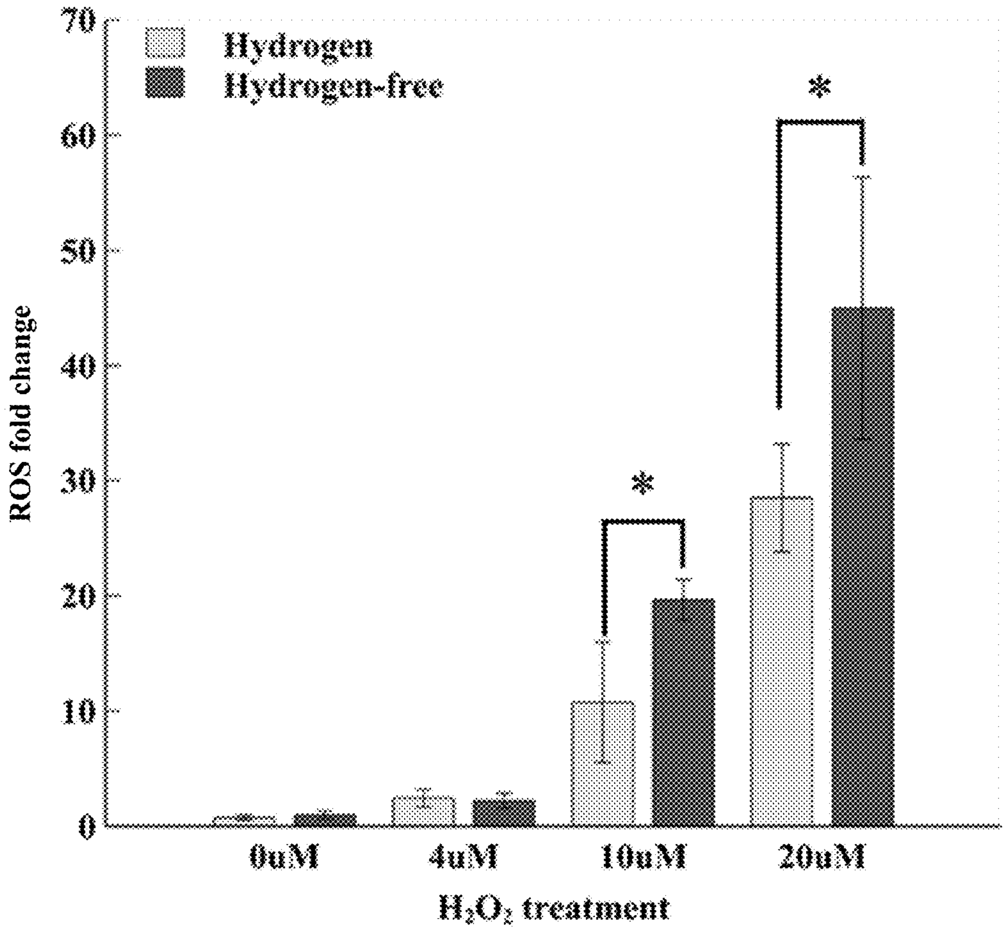
FIG. 7 shows a bar chart of the ROS fold change in the hydrogen group and in the hydrogen-free group after treatment with 0 μM $H_2O_2$, 4 μM $H_2O_2$, 10 μM $H_2O_2$, or 20 μM $H_2O_2$ according to embodiment 3 of the present invention (*t-test, $p<0.05$).

Two groups of cells infected with virus on part of the carrier sheets in the bioreactor were collected after 24 hours, and $H_2O_2$ with concentrations of 0 μM, 4 μM, 10 μM, and 20 μM was added to induce intracellular oxidation reaction, and the ROS fold changes were evaluated by the method of 2.3 in Example 2. As shown in FIG. 7, in the experimental group given molecular hydrogen, the intracellular oxidation reaction induced by $H_2O_2$ with concentration of 10 μM and 20 μM significantly reduced the ROS fold change, indicating that utilizing the electrolysis-based hydrogen generator to treat cell culture medium during virus mass production can significantly reduce the intracellular ROS stress.

3.2 Virus Yield

After the virus infection, the virus tier in the virus liquid was measured by the $TCID_{50}$ detection method after collecting the virus liquid in the bioreactors of the experimental group and the control group every day. The virus liquid was serially diluted 10-fold with MEM to $1/10^{10}$th of original concentration, and then inoculated into a 96-well cell culture plate at 100 μl/well (100 μl of cell fluid was already added to each well, containing $2\times10^4$ BHK21 cells), the BHK21 cells were cultured in a 5% $CO_2$ incubator at 37° C. for 3 days. After cytopathic effect (CPE) was observed and recorded, $TCID_{50}$ was calculated using the Reed-Muench method.

Figure 8A:
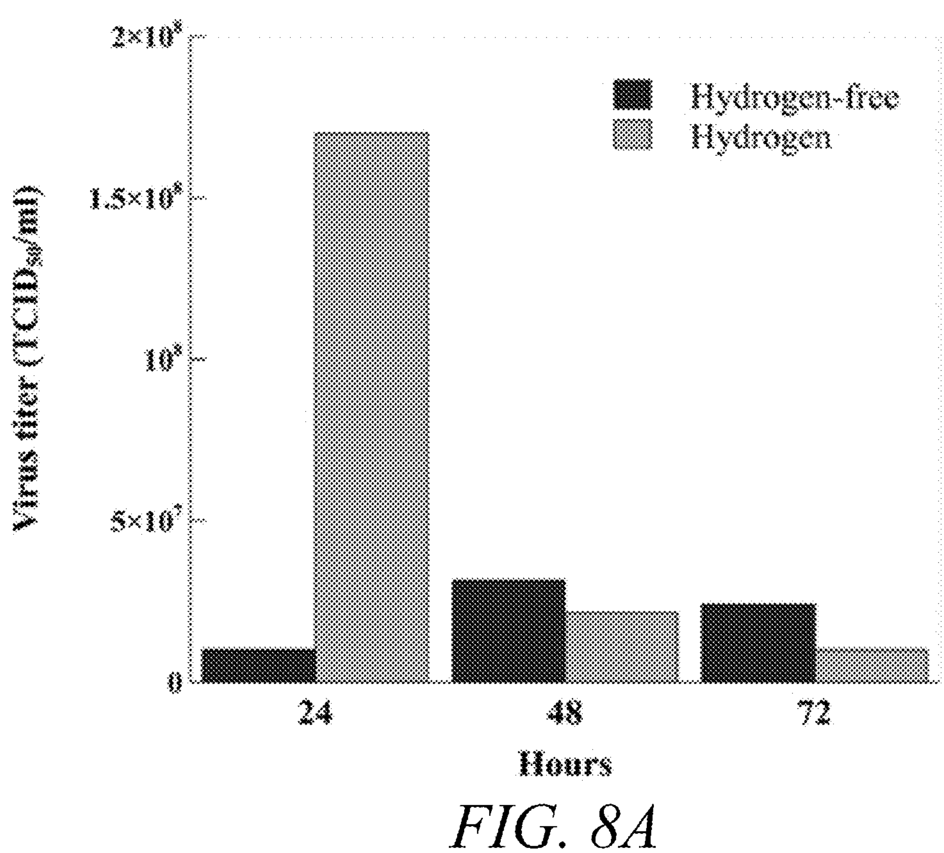
FIG. 8A shows a bar chart of the virus titer ($TCID_{50}$/ml) in the hydrogen group and in the hydrogen-free group according to embodiment 3 of the present invention. FIG.

As shown in FIG. 8A, the electrolysis-based hydrogen generator is used in the hydrogen group to provide hydrogen molecules to the cell culture medium, which can rapidly promote virus infection and release. After the virus infection, the virus yield in the hydrogen group reached 16 times more than that in the hydrogen-free group after 24 hours (the 4th day). If hydrogenation initiation (the 2nd day) to virus infection (the 3rd day) is regarded as the first stage, and virus infection to virus harvesting is regarded as the second stage, it may take 72 hours to harvest in the second stage for a typical virus culture, while the second stage of the embodiment of the present invention only takes 24 hours. Therefore, the culture method of the embodiment of the present invention can greatly shorten the time required for each batch of virus culture, and promote the virus production yield.

3.3 Cell Consumption Rate (Cell Death Rate)

Figure 8B:
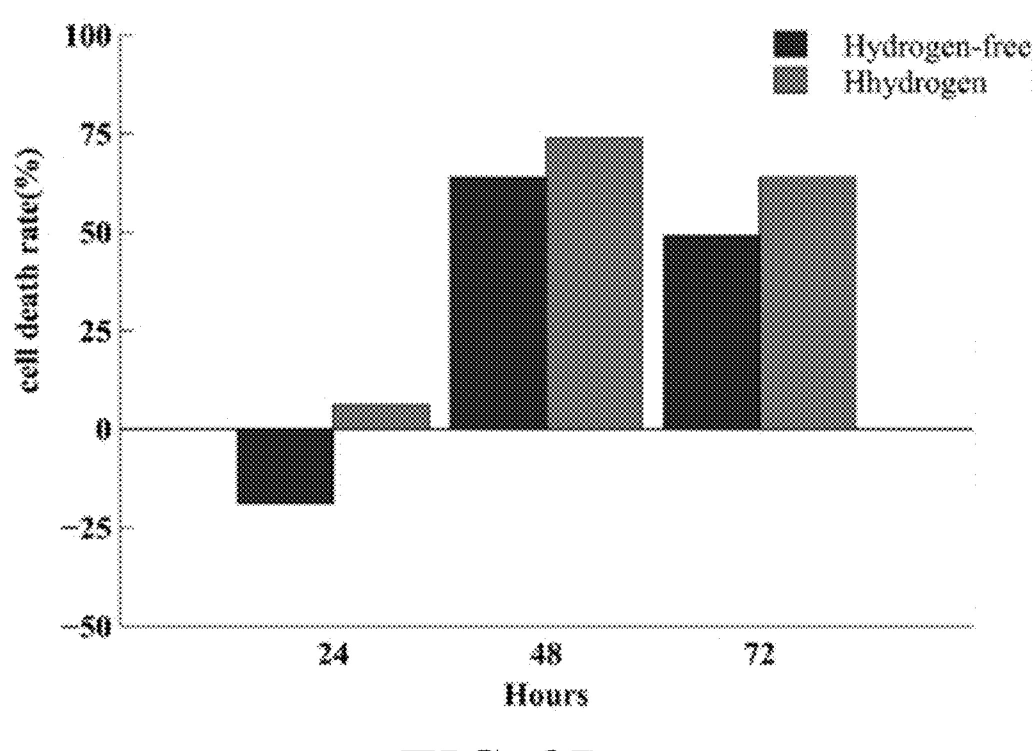

After virus infection, the cells on the carrier sheet in the bioreactors of the experimental group and the control group were collected every day, 1 ml of CVD was added, and the number of cells was calculated on that day. The formula for calculating the cell death rate is [(total number of cells on the previous day)−(total number of cells on that day)]/(total number of cells on the previous day)*100%. A high cell consumption rate indicates that the virus is using cells for replication, and a low cell consumption rate indicates that cells cannot be used by the virus for replication due to dormancy caused by high oxidative stress. As shown in FIG. 8B, it can be seen that at 24 hours after virus infection, the cell consumption rate of the experimental group is greater than that of the control group. The cell consumption rate in the control group at 24 hours was negative, indicating that the cells in the control group continued to increase at 24 hours after virus infection, while the cells in the experimental group died because they began to produce a large amount of virus. With FIG. 8A, it can be seen that the virus titers in the experimental group were significantly increased. The experimental group that was provided with molecular hydrogen was shown to accelerate viral antigen production by reducing the antiviral response associated with cellular aging.

3.4 Cellular Senescence Molecular Cdkn2a (p16) Expression

The expression level of the cellular senescence molecule Cdkn2a (p16) is an indicator of senescent cells. The increase on the expression level of Cdkn2a (p16) indicates that the cells tend to enter a senescent state, which can be used for evaluating the cellular aging state of the cells in the experimental group after being provided with hydrogen gas continuously. After the administration of hydrogen, the cells in the bioreactors of the experimental group and the control group were collected every day, and the cellular RNA in the samples was extracted with QIAzol lysis reagent (QIAGEN, Germany), and the SensiFAST™ cDNA Synthesis Kit (Bioline, Memphis, TN, USA) was used for converting cellular RNA into cDNA and performed quantitative PCR against cDNA with hamster Cdkn2a(p16) primer pair, the (Cdkn2a (p16) forward primer was listed as SEQ ID NO: 1 (5'-TCTTGGAAACTCTGGCGATA-3') and the (Cdkn2a(p16) reversing primer was listed as SEQ ID NO: 2 (5'-GAAGTTACGCCTGCCG-3'). Reference: Zeng Y J, Hsu M K, Tsai C A, Chu C Y, Wu H C, Wang H Y. A senescence-like cellular response inhibits bovine ephemeral fever virus proliferation. Vaccines. 2021; 9(6). doi: 10.3390/vaccines9060601).

The gene expression fold change of the senescence molecule Cdkn2a (p16) was analyzed using CFX Connect Real-Time PCR Detection System (Bio-Rad Laboratories, USA), and the gene expression fold change of the senescence molecule Cdkn2a (p16) gene (ΔΔCt) was calculated using the formula: $2^{-\Delta\Delta Ct}=2^{-(\Delta Ct\ experimental\ group-\Delta Ct\ control\ group)}$, ΔCt experimental group was the cycle threshold of cells in the experimental group, and ΔCt control group was the cycle threshold of cells in control group. The results are shown in FIG. 9. The fold change of the gene expression of the senescence molecule Cdkn2a (p16) decreased significantly after the hydrogen molecule was supplied on the third day, representing that the expression level of the senescence molecule p16 in the cells of the experimental group continuously provided with hydrogen molecules was decreased apparently compared with that in the cells of the control group. The reduced expression illustrates the efficacy of inhibiting cellular senescence when applied this device in a bioreactor.

The previously disclosed embodiments are merely illustrative of some preferred ones of the present invention, which are not intended to limit the scope thereof. Those who are skilled in the relevant technical fields can, after understanding the technical features and embodiments of the present invention as explained hereinabove, certainly make equivalent changes, alterations or modifications without departing from the spirit and scope of the present invention, which are nonetheless deemed as falling within the coverage of the present invention. Accordingly, the scope of the present invention to be protected by patent laws is subject to the definition of the claims attached to this specification.

What is claimed is:

1. An antioxidant culture method comprising:

providing a bioreactor containing cultured cells;

providing an electrolysis-based hydrogen generator comprising an anode, a cathode, and a septum between the anode and the cathode;

connecting the electrolysis-based hydrogen generator and the bioreactor;

inputting a culture medium of the bioreactor to the cathode and inputting a pure water to the anode; and providing a current to the electrolysis-based hydrogen generator to output a hydrogen from the cathode and dissolve the hydrogen in the culture medium of the bioreactor;

wherein the method is applied in a virus antigen manufacturing procedure.

2. The antioxidant culture method of claim 1, further comprising: measuring a hydrogen concentration of the culture medium, and raising an activation frequency of the current when the hydrogen concentration is lower than a default value.

3. The antioxidant culture method of claim 1, wherein an activation frequency of the current is 1 to 3 times per hour for more than 10 minutes each time.

4. The antioxidant culture method of claim 1, wherein a hydrogen concentration of the culture medium ranges from 0.1 to 1.6 ppm.

5. The antioxidant culture method of claim 1, wherein providing the current to the electrolysis-based hydrogen generator comprises two stages: a first stage before infection of virus and a second stage after infection of virus, wherein the first stage and the second stage have different activation frequency of the current.

6. The antioxidant culture method of claim 5, wherein the activation frequency of the current at the second stage is higher than that at the first stage.

7. The antioxidant culture method of claim 6, wherein the activation frequency of the current at the second stage is twice the activation frequency of the current at the first stage.

8. The antioxidant culture method of claim 7, wherein the activation frequency of the current at the first stage is once an hour for 15 minutes each time, and the activation frequency of the current at the second stage is twice an hour for 15 minutes each time.

9. The antioxidant culture method of claim 5, wherein a duration of the first stage is proportional to a duration of the second stage.

10. The antioxidant culture method of claim 9, wherein the duration of the first stage and the duration of the second stage are 1 day.

11. The antioxidant culture method of claim 1, wherein the bioreactor is a tidal bioreactor and a default value of hydrogen concentration is 0.7 ppm.

12. The antioxidant culture method of claim 1, wherein the current is a constant current and does not exceed 0.5 ampere.

13. The antioxidant culture method of claim 1, wherein providing an electrolysis-based hydrogen generator is implemented by connecting an auxiliary equipment with the bioreactor, wherein the auxiliary equipment comprises:

the electrolysis-based hydrogen generator, the cathode being connected with the bioreactor, and the culture medium of the bioreactor being inputted into the electrolysis-based hydrogen generator via a first pump and hydrogen gas being outputted from the cathode to the bioreactor;

a pure water supply end connected with the anode, pure water in the pure water supply end being inputted into the electrolysis-based hydrogen generator via a second pump; and a power control unit electrically connected with the electrolysis-based hydrogen generator for providing direct current to it and controlling the operation of the first pump and the second pump.

14. The antioxidant culture method of claim 13, wherein the cathode comprises a first pipeline and a second pipeline, the first pipeline and the second pipeline are connected with the bioreactor and the first pipeline is provided with the first pump, the second pipeline is used for outputting hydrogen gas, the anode comprises a third pipeline and a fourth pipeline, the third pipeline and the fourth pipeline are connected with the pure water supply end, the third pipeline is provided with a second pump and the fourth pipeline is used for outputting oxygen gas.

15. The antioxidant culture method of claim 13, wherein the cathode further comprises a cathode contact and the anode further comprises an anode contact, the anode contact and the cathode contact are electrically connected to the power control unit.

16. The antioxidant culture method of claim 15, wherein the power control unit comprises a power supply unit and a controller, a positive electrode of the power supply unit is electrically connected to the anode contact via the controller and the cathode contact is electrically connected to a negative electrode of the power supply unit, the controller is electrical connected with the first pump and the second pump.

17. The antioxidant culture method of claim 13, wherein the auxiliary equipment further comprises a hydrogen concentration detector which is arranged in the culture medium in the bioreactor and is connected to the power control unit for measuring the hydrogen concentration of the culture medium and adjusting the power control unit according to a comparison result of the hydrogen concentration of the culture medium and a default value.

18. The antioxidant culture method of claim 17, wherein the hydrogen concentration detector is a dissolved hydrogen meter.

19. The antioxidant culture method of claim 13, wherein the electrolysis-based hydrogen generator is a proton exchange membrane fuel cell, and the septum is a polymer membrane.

* * * * *

SEQUENCE LISTING

```
Sequence total quantity: 2
SEQ ID NO: 1          moltype = DNA  length = 20
FEATURE               Location/Qualifiers
```

-continued

```
source                  1..20
                        mol_type = other DNA
                        organism = synthetic construct
SEQUENCE: 1
tcttggaaac tctggcgata                                          20

SEQ ID NO: 2            moltype = DNA  length = 16
FEATURE                 Location/Qualifiers
source                  1..16
                        mol_type = other DNA
                        organism = synthetic construct
SEQUENCE: 2
gaagttacgc ctgccg                                              16
```